US008110809B2

United States Patent
Amano (10) Patent No.: US 8,110,809 B2
(45) Date of Patent: Feb. 7, 2012

(54) RADIATION DETECTOR AND RADIOGRAPHIC INSPECTION APPARATUS

(75) Inventor: Daizo Amano, Yokosuka (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 693 days.

(21) Appl. No.: 12/296,709

(22) PCT Filed: Apr. 23, 2007

(86) PCT No.: PCT/JP2007/058730
§ 371 (c)(1),
(2), (4) Date: Oct. 10, 2008

(87) PCT Pub. No.: WO2007/125862
PCT Pub. Date: Nov. 8, 2007

(65) Prior Publication Data
US 2009/0050816 A1 Feb. 26, 2009

(30) Foreign Application Priority Data
Apr. 28, 2006 (JP) ................................ 2006-124653

(51) Int. Cl.
*H01L 27/146* (2006.01)
*G01T 1/00* (2006.01)
*A61B 6/00* (2006.01)

(52) U.S. Cl. ........................ 250/370.09; 378/2; 378/19

(58) Field of Classification Search ............. 250/370.08, 250/370.09; 378/2, 19
See application file for complete search history.

(56) References Cited

U.S. PATENT DOCUMENTS

| 4,677,299 A | 6/1987 | Wong | |
|---|---|---|---|
| 7,541,593 B2* | 6/2009 | Yanagita et al. | 250/370.08 |
| 2003/0108147 A1* | 6/2003 | Kojima et al. | 378/19 |
| 2005/0067577 A1* | 3/2005 | Yanagita et al. | 250/370.09 |
| 2005/0230630 A1 | 10/2005 | Yanagita et al. | |

FOREIGN PATENT DOCUMENTS

| JP | 62-9405 | 1/1987 |
|---|---|---|
| JP | 62-095483 | 5/1987 |
| JP | 07-084052 | 3/1995 |
| JP | 2001-242253 | 9/2001 |
| JP | 2005-257437 | 9/2005 |

OTHER PUBLICATIONS

Japanese Office Action dated Mar. 16, 2010 with partial translation.

* cited by examiner

*Primary Examiner* — David Porta
*Assistant Examiner* — Faye Boosalis
(74) *Attorney, Agent, or Firm* — IPUSA, PLLC (57) ABSTRACT

On a wiring board 21, first and second semiconductor detection device arrays 22a and 22b are arranged along a depth direction (Y-axial direction). Each of the first and the second semiconductor detection device arrays 22a and 22b is composed by arranging six semiconductor detection devices $23_1$ through $23_6$ in one line in an arrangement direction (X-axial direction). Guard members 28a and 28b are arranged one on each end in the arrangement direction. In the semiconductor detection devices $23_1$ through $23_6$ of the first and the second semiconductor detection device arrays 22a and 22b, a kth (k is one of the number from 1 to 6) semiconductor detection device 23k from a reference line Xa is arranged by being shifted from others by ½ of a gap PT of the semiconductor detecting devices $23_1$ through $23_6$ in the arrangement direction.

8 Claims, 10 Drawing Sheets

|  | SPATIAL RESOLUTION IN THE CENTER | SPATIAL RESOLUTION AT Y:10mm | DETECTION EFFICIENCY |
|---|---|---|---|
| EXAMPLE OF EMBODIMENT | X:0.67mm<br>Y:0.58mm | X:0.80mm<br>Y:0.97mm | 1.8% |
| COMPARISON EXAMPLE 1 | X:0.66mm<br>Y:0.66mm | X:0.60mm<br>Y:1.57mm | 1.8% |
| COMPARISON EXAMPLE 2 | X:0.71mm<br>Y:0.68mm | X:0.63mm<br>Y:0.79mm | 0.9% |

RADIATION DETECTOR AND RADIOGRAPHIC INSPECTION APPARATUS

TECHNICAL FIELD

The present invention generally relates to radiation detectors and radiographic inspection apparatuses. More specifically, the present invention relates to a radiation detector configured to detect gamma rays emitted from a radioisotope situated in a subject and a radiographic inspection apparatus.

BACKGROUND ART

Recently, tomography apparatuses have been widely used in order to obtain information of the inside of a living organism (subject). There are an X-ray computed tomography (hereinafter "X-ray CT") apparatus, a magnetic resonance imaging (MRI) apparatus, a single photon emission CT (hereinafter "SPECT") apparatus, and a positron emission tomography (hereinafter "PET") apparatus, as the tomography apparatuses. In the X-ray CT apparatus, X-ray beams having narrow widths are emitted to a certain cross section of the subject in multiple directions, X-rays penetrating through the subject are detected, and a spatial distribution of the degree of abruption of the X-rays in the cross section is computed by a computer and imaged. Thus, dysplasia inside the subject such as a hemorrhagic area can be recognized by the X-ray CT.

On the other hand, since functional information in the subject can be obtained with high precision by the PET apparatus, development of the PET apparatuses has been progressing recently. In a diagnostic method using the PET apparatus, first, a medicine for inspection which is supplied with a positron nuclide is introduced inside the subject by an injection, inhalation, or the like. The medicine for inspection introduced in the subject is stored in a specific portion having a function corresponding to the medicine for inspection. For example, in a case where a medicine for inspection of saccharide is used, the medicine is selectively stored in a portion where metabolism of a cancer cell or the like frequently occurs. At this time, a positron radiates from the positron nuclide of the medicine for inspection. At the time when the positron and an electron in the periphery of the positron are coupled and annihilated, two gamma rays (so-called annihilation gamma rays) are radiated in directions approximately 180 degrees relative to each other. These two gamma rays are simultaneously detected by a radiation detector provided surrounding the subject and an image is regenerated by a computer or the like, so that image data of the distribution of the radioisotopes (RI) of the subject are obtained. Thus, in the PET apparatus, since the functional information about the body of the subject is obtained, it is possible to elucidate the pathology of various intractable diseases.

Figure 1:
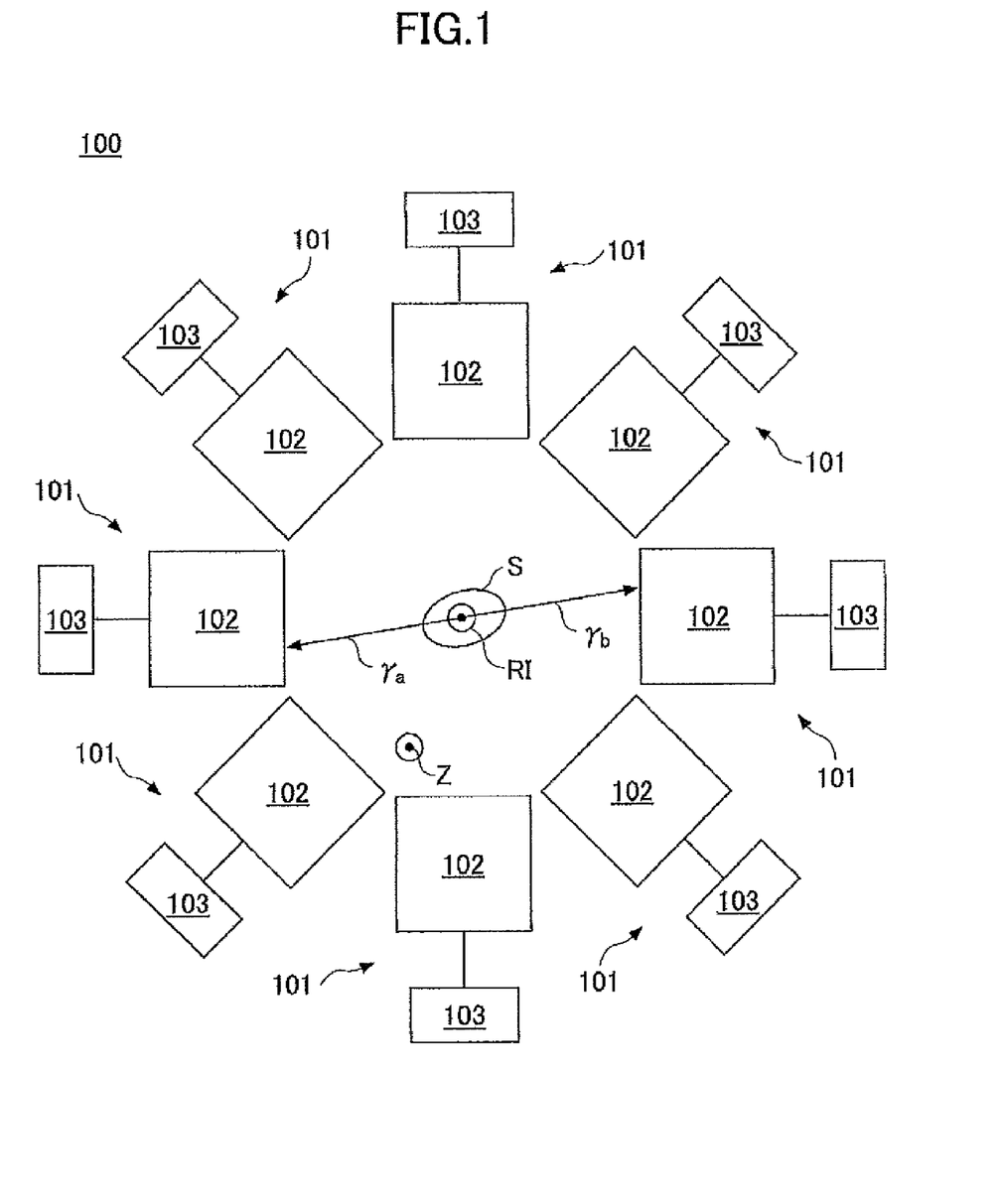
FIG. 1 is a schematic structural view of a PET apparatus.

FIG. 1 is a schematic structural view of a PET apparatus. As shown in FIG. 1, in a PET apparatus 100, gamma ray detectors 101 are provided so as to surround a subject S 360 degrees. The gamma ray detector 101 includes a semiconductor detector 102 and a detection circuit 103. The semiconductor detector 102 includes a semiconductor detection device array (see FIG. 2) where semiconductor detection devices 104 (see FIG. 2) are arranged. The detection circuit 103 is configured to detect the gamma rays entering the semiconductor detection devices 104. In addition, a generating position of each gamma ray is identified based on an output signal from the detection circuit 103 indicating that the gamma ray has entered and position information of the semiconductor detection device 104 indicating where the gamma ray has entered. Furthermore, by detecting multiple gamma rays emitted in random directions, an image of the distribution of the medicine for inspection in the subject S is regenerated.

Thus, the X-ray CT apparatus or the PET apparatus configured to detect radiation such as the X-rays or the gamma rays so that pathological analysis is performed includes multiple semiconductor detection devices in order to improve detection efficiency, namely the amount or the number of radiations detected per unit time (for example, see Patent Document 1).

[Patent Document 1] Japanese Patent Application Publication No. 2001-242253

DISCLOSURE OF THE INVENTION

Problems to be Solved by the Invention

Figure 2:
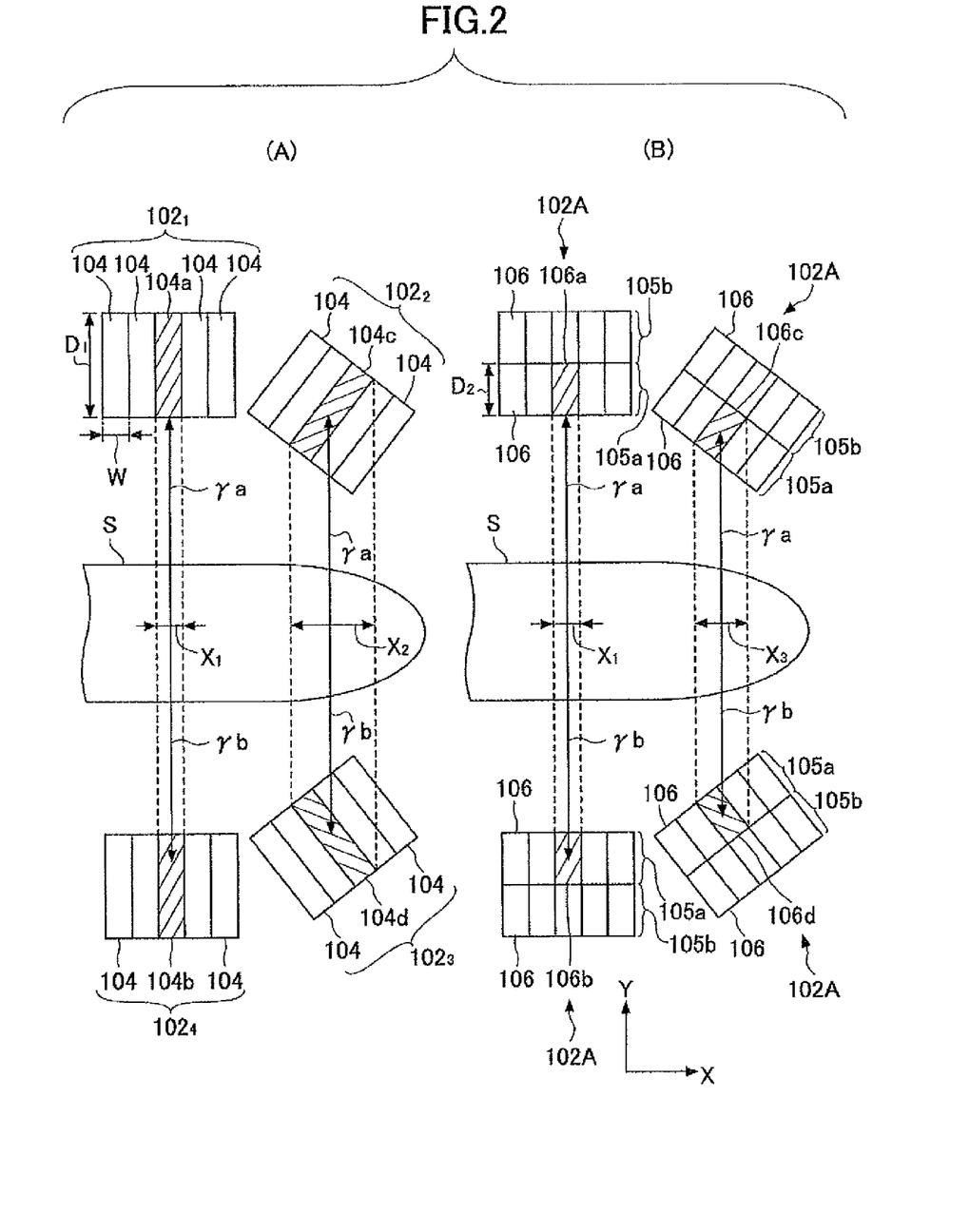
FIG. 2 is a view for explaining problems of the conventional semiconductor detector.

In the meantime, the semiconductor detection device array 102 is arranged in a surface perpendicular to a body axis of the subject S parallel with a Z-axis shown in FIG. 1. FIG. 2 shows a semiconductor detector 102 of a part of the PET apparatus. In an example shown in FIG. 2(A), each semiconductor detection device array 102 includes five semiconductor detection devices 104. The semiconductor detection devices 104 are arranged so as to face the subject S. Each semiconductor detection device 104 has a width W which is in the arrangement direction and a depth $D_1$ which is along a direction where the subject S and the semiconductor detection device array 102 are visually connected to each other.

Referring to FIG. 2(A), it is general practice that the resolution of the entrance position of the gamma ray is improved more as the width W of the semiconductor detection devices 104 is made smaller. Because of this, it is possible to precisely identify a position where the gamma ray is generated, namely a position of the medicine for inspection in the subject S, so that spatial resolution is improved. For example, as shown at the left side in FIG. 2(A), in a case where gamma rays γa and γb enter the semiconductor detection devices 104a and 104b of the semiconductor detection device arrays $102_1$ and $102_4$, respectively, from a front surface and are detected, that is, in a case where the gamma rays γa and γb enter from the center of a visual field range of the semiconductor detection devices 104a and 104b, a range in an X-axial direction of a position where the gamma ray is generated is $X_1$. The range $X_1$ becomes smaller as the width W is made smaller.

However, as shown at the right side in FIG. 2(A), in a case where gamma rays γa and γb obliquely enter the semiconductor detection device 104c and 104d of the semiconductor detection device array $102_2$ and $102_3$, respectively, and are detected, that is, in a case where the gamma rays γa and γb enter from the periphery of the visual field range of the semiconductor detection device 104c and 104d, a range in an X-axial direction of a position where the gamma ray is generated is $X_2$. The range $X_2$ is not reduced as the width W is made smaller and is much greater than the above-mentioned range $X_1$. In other words, even if the width W is made narrow, it is difficult to sufficiently improve the spatial resolution in the case where the gamma rays γa and γb enter from the periphery of the visual field range of the semiconductor detection device 104.

The problem where a decrease of the spatial resolution in the periphery of the visual field range of the semiconductor detection device 104 can be solved by making the depth $D_1$ of the semiconductor detection device 104 short. For example, as shown in a semiconductor detection device array 105a of FIG. 2(B), the depth $D_2$ of the semiconductor detection device 106 is made, for example, one half of the depth $D_1$ of the semiconductor detection device 104 shown in FIG. 2(A).

As a result of this, as shown at the right side in FIG. 2(B), in a case where gamma rays γa and γb obliquely enter the semiconductor detection device 106c and 106d, respectively, of the semiconductor detection device array 105a and are detected, that is, in a case where the gamma rays γa and γb enter from the periphery of the visual field range of the semiconductor detection devices 106c and 106d, a range in an X-axial direction of a position where the gamma ray is generated is $X_3$. The range $X_3$ is smaller than the above-mentioned range $X_2$ shown in FIG. 2(A). Therefore, the spatial resolution in the periphery of the visual field range is improved. It should be noted that the spatial resolution in the center part of the visual field in this case is the range $X_1$ as shown at the left side in FIG. 2(B) which is equivalent to the case shown at the left side in FIG. 2(A).

In the meantime, a phenomenon where the entered gamma ray generates an electron-hole pair is probabilistic. Accordingly, because the semiconductor detection device 105 has a depth shorter that that of the semiconductor detection device 104, the frequency where the electron-hole pair is generated in the semiconductor detection device 105 is reduced so that the detection efficiency of the gamma ray is decreased compared to the semiconductor detection device 104. Because of this, as shown in FIG. 2(B), two lines are formed by the semiconductor detection device arrays 105a and 105b in the depth direction so that the detection efficiency is maintained.

However, in this case, while the semiconductor detector 102A having the semiconductor detection device arrays 105a and 105b maintains the detection efficiency and good spatial resolution in the entire visual field, the number of the semiconductor detection devices 105 is twice that of the case shown in FIG. 2(A). As a result of this, the number of detection circuits connected to the semiconductor detection devices 105 and the number of downstream circuits become double. This causes an increase of the assembly cost in addition to the material cost so that the manufacturing cost is drastically increased.

Means for Solving Problems

Accordingly, embodiments of the present invention may provide a novel and useful radiation detector and radiographic inspection apparatus solving one or more of the problems discussed above.

More specifically, the embodiments of the present invention may provide a radiation detector whereby the detection efficiency of the radiation can be maintained, good spatial resolution is provided in the entire field of view of the semiconductor detector, and an increase of the manufacturing cost can be prevented; and may also provide a radiographic inspection apparatus using the radiation detector.

One aspect of the present invention may be to provide a radiation detector, including: a semiconductor detector including a plurality of semiconductor detection devices configured to generate electron-hole pairs based on entry of the radiation, wherein the semiconductor detector included n number of semiconductor detection device arrays provided on a board, the plural semiconductor detection devices are arranged in a first direction with a designated gap, the n number of the semiconductor detection device arrays are arranged in a second direction perpendicular to the first direction to form a $1^{st}$ line through an nth line, and the semiconductor detection device arrays of the $1^{st}$ line through the nth line are shifted at any of 0, 1/n, . . . , (n−1)/n of the designated gap from a reference position in the first direction, where n is an integer number and equal to or greater than 2.

Another aspect of the present invention may be to provide a radiographic inspection apparatus, including: the above-mentioned radiation detector being configured to detect radiation generated from a subject including a radioisotope; and to provide an information processing part configured to obtain distribution information of the radioisotope in the subject based on detection information, the detection information including entry time and entry position of the radiation obtained from the radiation detector.

Other objects, features, and advantages of the present invention will become more apparent from the following detailed description when read in conjunction with the accompanying drawings.

Effect of the Invention

According to the embodiment of the present invention, it is possible to provide a radiation detector whereby the detection efficiency of the radiation can be maintained, good spatial resolution is provided in the entire field of view of the semiconductor detector, and an increase of the manufacturing cost can be prevented; and to provide a radiographic inspection apparatus using the radiation detector.

EXPLANATION OF REFERENCE SIGNS

10 PET apparatus
11 and $11_1$ through $11_8$ detector
12 information processing part
13 display part
14 control part
15 input and output part
20, 40, and 50 semiconductor detector
21 wiring board
22 and $22_1$ through $22_n$ semiconductor detection device array
22a first semiconductor detection device array
22b second semiconductor detection device array
23 and $23_1$ through $23_6$ semiconductor detection device
24 semiconductor crystalline substrate
24a entrance surface
24b and 24c groove part 25 first electrode
26 second electrode
27 conductive adhesion layer
28a, 28b, $28_1$ through $28_n$ guard member
29 connector
30 detection circuit
PT gap in arrangement direction of semiconductor detection device

BEST MODE FOR CARRYING OUT THE INVENTION

A description is given below, with reference to FIG. 3 through FIG. 11 of embodiments of the present invention.

First Embodiment

Figure 3:
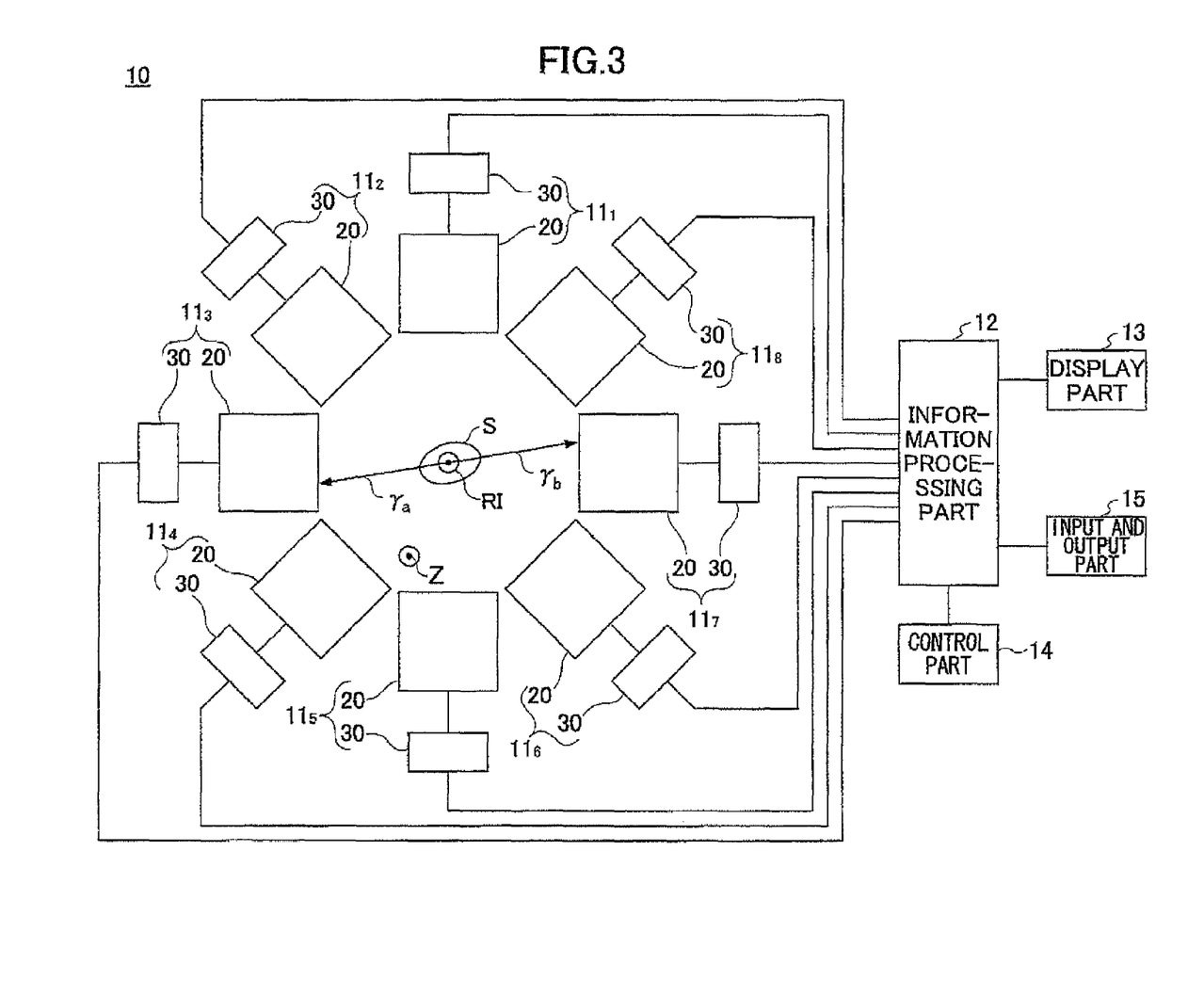
FIG. 3 is a block diagram showing a structure of a PET apparatus of a first embodiment of the present invention.

FIG. 3 is a block diagram showing the structure of a PET apparatus of a first embodiment of the present invention.

As shown in FIG. 3, a PET apparatus 10 includes radiation detectors 11, an information processing part 12, a display part 13, a control part 14, an input/output part 15, and others. The radiation detectors 11 are provided surrounding a subject S and configured to detect gamma rays. The information processing part 12 is configured to process detection data from the radiation detectors 11 and regenerate image data of a position of a positron nuclide RI in the body of the subject. The display part 13 is configured to display the image data and other data. The control part 14 is configured to control movement of the radiation detectors 11 and the subject S and other parts. The input/output part 15 is, for example, a terminal configured to transmit instructions to the image processing part 12 or the control part 14, or a printer configured to output the image data.

The radiation detectors 11 include semiconductor detectors 20 and detection circuits 30. The semiconductor detectors 20 are arranged so that entrance surfaces of gamma rays γa and γb face toward the subject S. A medicine for inspection identified by the positron nuclide RI is introduced in the subject S in advance.

When a positron generated from the positron nuclide RI is annihilated, two gamma rays $\gamma_a$ and $\gamma_b$ are simultaneously generated. The semiconductor detectors 20 detect the gamma rays $\gamma_a$ and $\gamma_b$. Since two gamma rays $\gamma_a$ and $\gamma_b$ are radiated in directions substantially 180 degrees relative to each other, the gamma rays $\gamma_a$ and $\gamma_b$ enter semiconductor detectors 20 of the radiation detectors 11 facing each other via the subject S. Each of the semiconductor detectors 20, where one of the gamma rays $\gamma_a$ and $\gamma_b$ enters, transmits an electric signal (detection signal), generated by entry of the one of the gamma rays $\gamma_a$ and $\gamma_b$, to the corresponding detection circuit 30.

The detection circuit 30 is configured to determine a time (entry time) when the one of the gamma rays $\gamma_a$ and $\gamma_b$ enters the radiation detector 11 based on the detection signal supplied from the semiconductor detector 20. In addition, the detection circuit 30 transmits detection data to the information processing part 12. The detection circuit 30 includes, for example, an analog ASIC and a digital ASIC. The analog ASIC is configured to calculate the entry type based on the detection signal which is an analog signal. The digital ASIC is configured to transmit the entry time and entry position as digital data to the information processing part 12.

The information processing part 12 is configured, based on the detection data, to regenerate image data by detection of coincidence and use of an image regenerating algorithm. In the detection of the coincidence, if there are two or more detected data elements whose entry times are substantially the same, the detection data are determined as valid data so as to be regarded as coincident data. If the gamma ray entry times are not the same, the detected data elements are determined as invalid data so as to be discarded. In addition, the image data are regenerated from the coincidence information, a detection element number or the like included in the coincidence information, the position information of the detection element corresponding to this, and other data, based on an image regenerating algorithm such as an expectation maximization method. The display part 13 is configured to display the regenerated image data based on a request of the input/output part 15. Detection of the coincidence and the image regeneration algorithm are not limited to the above-mentioned example. Methods known to the public may be applied to the detection of the coincidence and the image regeneration algorithm.

With the above-mentioned structure and operation, the PET apparatus 10 detects gamma rays from the positron nuclide RI selectively positioned in the body of the subject S so as to regenerate the image data of the positron nuclide RI distribution. Details of the radiation detector 11 are discussed below.

The radiation detectors $11_1$ through $11_8$ of the Pet apparatus 100 are arranged 360 degrees around the subject S. Each of the radiation detectors $11_1$ through $11_8$ includes one of the semiconductor detectors 20 situated at the subject S side. Here, an axial direction of the subject S is defined as a Z-axial direction (Z and −Z directions). The radiation detector 11 may be provided so as to move in the Z-axial directions relative to the subject S. While eight radiation detectors $11_1$ through $11_8$ are shown in FIG. 3, the present invention is not limited to this. The number of the radiation detectors 11 can be properly selected.

Figure 4:
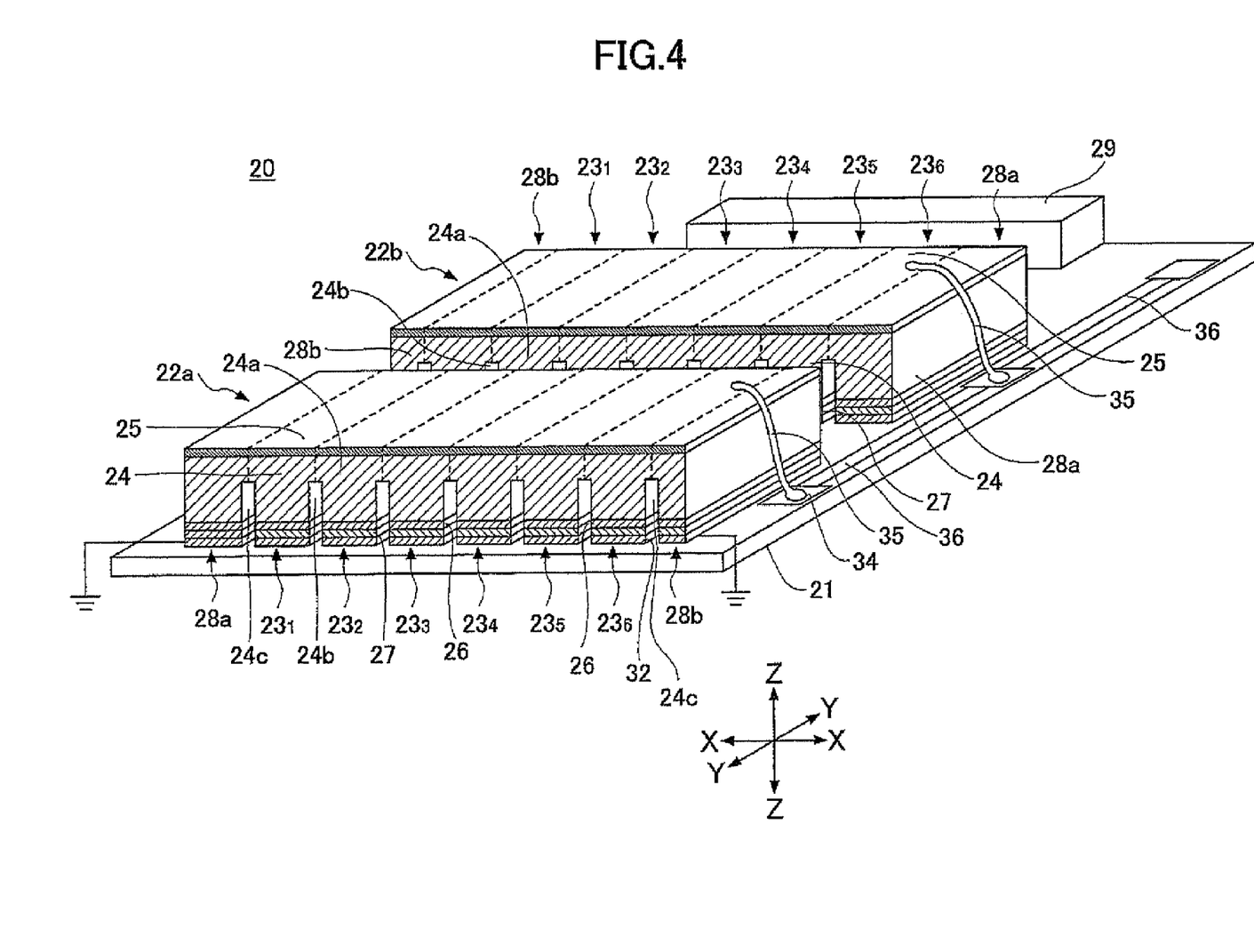
FIG. 4 is a perspective view showing a structure of a semiconductor detector.
Figure 5:
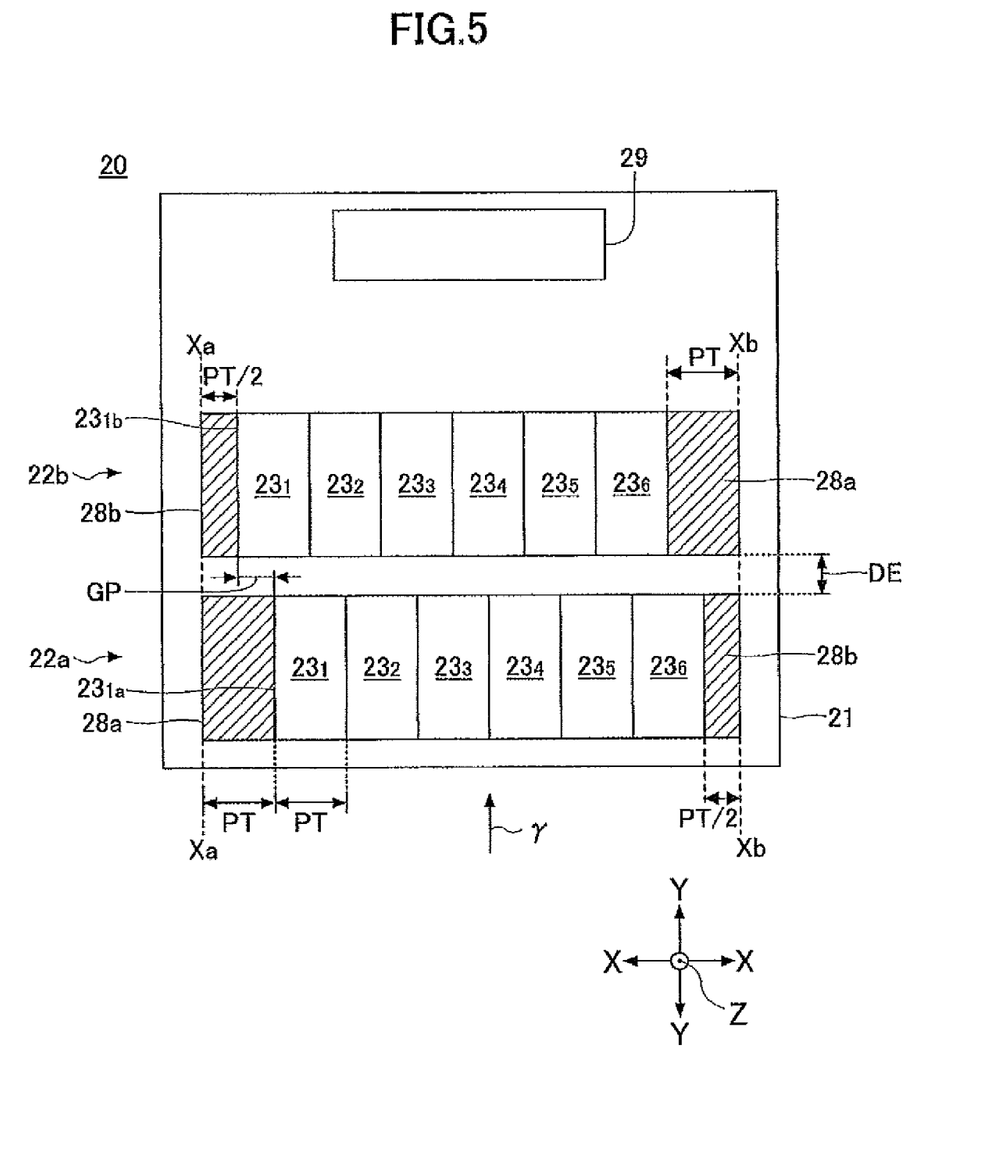
FIG. 5 is a schematic plan view of the semiconductor detector.
Figure 6:
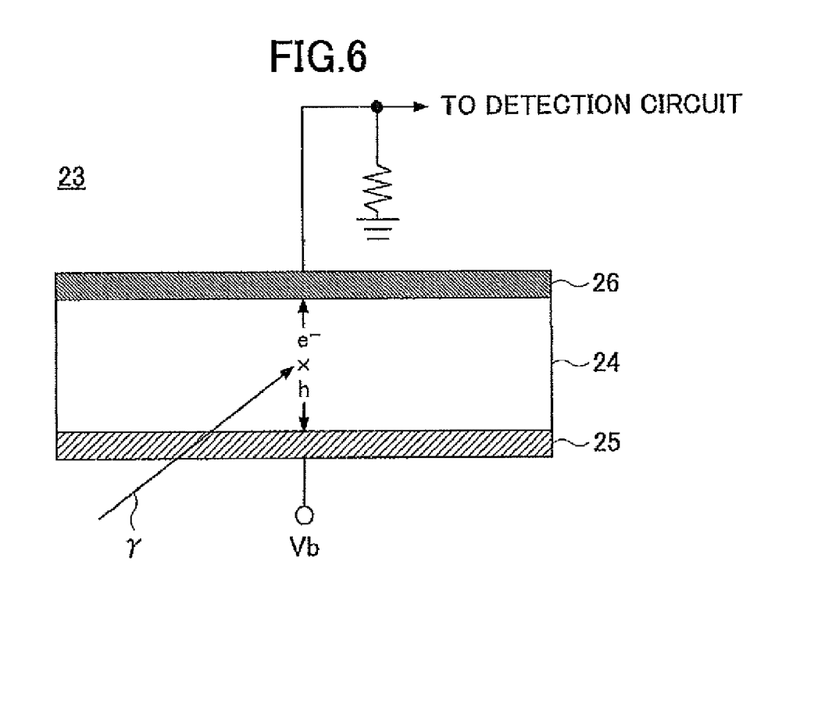
FIG. 6 is a view for explaining operations of the semiconductor detection device.

FIG. 4 is a perspective view showing the structure of the semiconductor detector 20 and shows the semiconductor detector 20 seen from the substantially entry side of the gamma ray. FIG. 5 is a schematic plan view of the semiconductor detector 20. FIG. 6 is a view for explaining operations of the semiconductor detection device 23.

Referring to FIG. 4 through FIG. 6, the semiconductor detector 20 includes a wiring board 21, two semiconductor detection device arrays 22a and 22b, a connector 29, and others. The semiconductor detection device arrays 22a and 22b are arranged on the wiring board 21. The connector 29 is configured to transmit the output of the semiconductor detector 20 to the detection circuit 30 shown in FIG. 3. In each of the semiconductor detection device arrays 22a and 22b, a first electrode 25 and a second electrode 26 are provided one on each of two surfaces perpendicular in an Z-axial direction of a substantially planar plate-shaped semiconductor crystalline substrate 24. Each of the semiconductor detection device arrays 22a and 22b includes semiconductor detection devices $23_1$ through $23_6$, guard members 28a and 28b, and others. The semiconductor detection devices $23_1$ through $23_6$ are formed by dividing the semiconductor crystalline substrate 24 in the X-axial direction by groove parts 24b formed in the second electrode 26 side surface in the Y-axial direction. The guard members 28a and 28b are provided one on each side (outside in the X-axial direction) in the arrangement direction of the semiconductor detection devices $23_1$ through $23_6$. The semiconductor crystalline substrate 24 and the guard members 28a and 28b are made of the same material and are formed in a body. Although dividing positions between the neighboring semiconductor detection devices $23_1$ through $23_6$ are indicated by dotted lines or solid lines in FIG. 4 and FIG. 5, the dividing positions pass through the center in the X-axial direction of the grooves parts 24b and extend in the Y-axial direction. The gap of the neighboring semiconductor detection devices $23_1$ through $23_6$ corresponds to the distance between the neighboring dividing positions.

In the example shown in FIG. 4, directions where the semiconductor detection devices $23_1$ through $23_6$ are aligned are called arrangement directions (X-axial directions). Directions where the semiconductor detection device arrays 22a and 22b are aligned are called depth directions (Y-axial directions). Directions where the wiring board 21 and the semiconductor detection device arrays 22a and 22b are called stacking directions (Z-axial directions). In addition, although each of the semiconductor detection device arrays 22a and 22b includes six semiconductor detection devices $23_1$ through $23_6$ in the example shown in FIG. 4, the number of the semiconductor detection devices 23 is not limited to this example. As long as the number of the semiconductor detection device is equal to or greater than two, there is no limitation to the number of the semiconductor detection devices 23.

Each semiconductor detection device $23_1$ through $23_6$ includes the semiconductor crystalline substrate 24, the first electrode 25, and the second electrode 26, and others. The first electrode 25 is formed on an upper surface of the semiconductor crystalline substrate 24. The second electrodes 26 are formed on the lower surface of the semiconductor crystalline substrate 24.

The semiconductor crystalline substrate 24 is made of, for example, cadmium telluride (CdTe) which is sensitive to gamma rays having energy levels of 511 keV, $Cd_{1-x}Zn_xTe$ (CZT), thallium bromide (TlBr), silicon, or the like. A dopant for controlling conductivity may be included in these materials. Silicon is preferable as a material of the semiconductor crystalline substrate 24 because silicon has a higher mechanical strength than CdTe and a crystal defect may not be formed in silicon during processing. It is normal practice that a dopant is contained in the semiconductor crystalline substrate 24 in order to control the conductivity of the semiconductor crystalline substrate 24. For example, in a case where the semiconductor crystalline substrate 24 is made of cadmium telluride (CdTe), a p-type dopant is introduced in the semiconductor crystalline substrate 24.

The semiconductor crystalline substrate 24 of any of the semiconductor detection devices $23_1$ through $23_6$ has the same width, depth, and thickness. The semiconductor crystalline substrate 24 has, for example, 1.2 mm width (X-axial direction), 5 mm depth (Y-axial direction), and approximately 1 mm thickness. Semiconductor crystal is formed by a Bridgman method which is a crystal growth method of the semiconductor or a moving heating method and the semiconductor crystal is cut in a designated crystal orientation and in a planar plate manner so that the semiconductor crystalline substrate 24 is obtained.

The first electrode 25 is made of a conductive film which substantially covers the upper surface of the semiconductor crystalline substrate 24. A negative bias voltage Vb is applied to the first electrode 25 so that the first electrode 25 becomes a cathode. In a case where the semiconductor crystalline substrate 24 is made of CdTe, the first electrode 25 is made of, for example, platinum (Pt). The bias voltage Vb is, for example, −60 V through −1000 V DC. The first electrode 25 is continuously formed on the entire upper surfaces of the six semiconductor crystalline substrates 24a. Although the first electrode 25 covers the upper surfaces of the guard members 28a and 28b in the example shown in FIG. 4, this is not mandatory. The bias voltages Vb is applied from outside of the wiring board 21 via the wiring pattern 36 and the wiring 35.

The second electrode 26 is made of a conductive film which substantially covers the lower surfaces of the six semiconductor crystalline substrate 24a between the groove parts 24b. The second electrode 26 functions as an anode. In (indium) is applied to the semiconductor crystalline substrate 24 at the second electrode 26 side. If the semiconductor crystalline substrate 24 is made of CdTe, gold (Au) is used as the second electrode 26. One of the second electrodes 26 is provided for each of the semiconductor detection devices $23_1$ through $23_6$ and neighboring second electrodes 26 are electrically insulated from each other. The second electrodes 26 are electrically connected to the connector 29 via the corresponding conductive adhesion layers 27, the pad electrodes 32 and wiring patterns (not shown in FIG. 4) provided on the wiring board 21.

The second electrodes 26 are formed on lower surfaces of the guard members 28a and 28b and connected to electrical ground via the conductive adhesive layer 27 and the pad electrode 32. With this structure, the electron-hole pairs generated by the gamma rays entering the guard members 28a and 28b flow to the voltage for the substrate and source so that mixing noise into the detection signal can be avoided. The above-discussed structure of the lower surfaces of the guard members 28a and 28b are not mandatory. If the guard members are made of materials other than the semiconductor crystalline substrate, the above-discussed structure of the lower surfaces of the guard members 28a and 28b are not necessary.

The conductive adhesion layer 27 is made of a carbon filler or metal powder selected from a group consisting of gold (Au), silver (Ag), copper (Cu) or an alloy thereof and a conductive adhesive made of resin. For example, a conductive paste or an anisotropic adhesive can be used as the conductive adhesion layer 27.

As shown in FIG. 6, in the semiconductor detection device 23, when the gamma ray γ enters the semiconductor crystalline substrate 24, electron-hole pairs whose number corresponds to the energy of the gamma ray γ are generated. Since an electric field is applied from the second electrode 26 into the semiconductor crystalline substrate 24 in the direction of the first electrode 25, electron holes are attracted to the first electrode 25 and electrons are attracted to the second electrode 26. Because of this, the detection signal is generated so as to be transmitted to the detection circuit 30. Even if a gamma ray γ enters the semiconductor crystalline substrate 24, generation of the electron-hole pair is probabilistic. The electron-hole pairs may not be generated in the semiconductor crystalline substrate 24 so that the gamma ray may exit the semiconductor crystalline substrate 24.

Referring back to FIG. 4 and FIG. 5, the guard members 28a and 28b are provided one at each end in the arrangement direction of the semiconductor detection device arrays 22a and 22b so as to protect the outside surfaces of the semiconductor detection devices $23_1$ and $23_6$. As long as the material of the guard members 28a and 28b does not make the first electrode 25 and the second electrode 26 electrically conductive, there is no limitation in the materials of guard members 28a and 28b. However, it is preferable that the materials of the guard members 28a and 28b are the same as the material of the semiconductor crystalline substrate 24 as long an adverse influence due to the stress based on the difference of coefficients of thermal expansion by heating in the manufacturing process can be avoided. It is more preferable that the guard members 28a and 28b be made of the same and continuous crystalline substrate as the semiconductor crystalline substrate 24. Because of this, it is not necessary to adhere the guard members 28a and 28b to the semiconductor crystalline substrate 24 so that a forming process of the guard members 28a and 28b can be simplified. It is preferable to form groove parts 24c between the guard member 28a and the semiconductor detection device $23_1$ and between the guard member 28b and the semiconductor detection device $23_6$. Because of this, it is possible to avoid flow-in of the electron-hole pairs generated by the gamma ray entering the guard members 28a and 28b to the second electrodes 26 of the neighboring semiconductor detection devices $23_1$ and $23_6$. The groove parts 24c may have the same configuration as the groove parts 24b. The widths of the guard members 28a and 28b are determined based on the gaps of the semiconductor detection devices $23_1$ through $23_6$ discussed below.

While the semiconductor detection device arrays 22a and 22b have the above-discussed structures, the arrangement of the semiconductor detection device arrays 22a and 22b on the wiring board 21 are different as shown in FIG. 5. In the following explanations, a semiconductor detection device array arranged at a side where the gamma ray γ enters is called a first semiconductor detection device array 22a, and a semiconductor detection device array arranged at a deep side is called a second semiconductor detection device array 22b. In a case where it is not necessary to distinguish both arrays, the arrays are simply called the semiconductor detection device arrays 22a and 22b.

In this embodiment, positional relationships of the semiconductor detection devices 23 of the first semiconductor detection device array 22a and the second semiconductor detection device array 22b are characteristic. The semiconductor detection devices 23 of the first semiconductor detection device array 22a and the second semiconductor detection device array 22b are arranged with a designated gap PT in the arrangement direction (X-axial direction). In addition, a left side surface $23_{1a}$ of the semiconductor detection device $23_1$ of the first semiconductor detection device array 22a is situated with a gap PT from a reference line Xa-Xa (see FIG. 5). On the other hand, a left side surface $23_{1b}$ of the semiconductor detection device $23_1$ of the second semiconductor detection device array 22b is situated with a gap PT/2 from the reference line Xa-Xa (see FIG. 5). Thus, each of the semiconductor detection devices $23_1$ through $23_6$ of the first semiconductor detection device array 22a and the each of the semiconductor detection devices $23_1$ through $23_6$ of the second semiconductor detection device array 22b are shifted from each other by PT/2 in the arrangement direction.

In addition, the guard member 28a situated at the left end of the first semiconductor detection device array 22a has the same width as the gap PT and the guard member 28b situated at the right end of the first semiconductor detection device array 22a has the same width as the gap PT/2. On the other hand, the guard member 28b situated at the left end of the second semiconductor detection device array 22b has the same width as the gap PT/2 and the guard member 28a situated at the right end of the second semiconductor detection device array 22b has the same width as the gap PT. Thus, by providing the guard members 28a and 28b, the width (length of the arrangement direction) of the semiconductor detection device array 22a is equal to that of the semiconductor detection device array 22b. The semiconductor detection device arrays 22a and 22b are arranged so that left ends of the semiconductor detection device arrays 22a and 22b are situated in positions the same as the reference line Xa-Xa. With this structure, in the assembling process of the semiconductor detector 20, when the semiconductor detection device arrays 22a and 22b are arranged, it is easy to position the semiconductor detection device arrays 22a and 22b to make the semiconductor detection devices $23_1$ through $23_6$ have the above-discussed positional relationships. Although it is preferable to provide the guard members 28a and 28b, the guard members 28a and 28b are not mandatory in the present invention.

Although positioning is performed by using the end parts of the left ends of the semiconductor detection devices 22a and 22b in the above-discussed example, the positioning may be performed by using the right ends at the reference line Xb-Xb.

Thus, the semiconductor detection device arrays 22a and 22b are arranged in the depth direction by shifting in the arrangement direction ½ of the gap of the semiconductor detection devices $23_1$ through $23_6$. As a result of this, the spatial resolution in the center of the visual field of the semiconductor detector 20, namely the gamma ray entering from the substantially front surface of the semiconductor detector 20, is improved compared to the spatial resolution of the center of the visual field in a case where a single semiconductor detection device array 22 is provided, and is substantially equal to the spatial resolution in the center of the visual field of the semiconductor detector 20 in a case where the width of the semiconductor detection devices 23 is made half.

In addition, the semiconductor detection device arrays 22a and 22b are arranged in the depth direction (Y-axial direction). Each of the semiconductor detection device arrays 22a and 22b in this example is shorter than for a case where a single semiconductor detection device array 22 is provided and the depth of the semiconductor detection device array 22 is substantially equal to the sum of the depths of the semiconductor detection device arrays 22a and 22b. Because of this, as discussed with reference to FIG. 2(B), it is possible to improve the spatial resolution of the peripheral part of the visual field of the semiconductor detector 20.

In addition, the detection efficiency of the semiconductor detector 20 in this example is substantially equal to that in the case where a single semiconductor detection device array 22 is provided and the depth of the semiconductor detection device array 22 is substantially equal to the sum of the depths of the semiconductor detection device arrays 22a and 22b, and therefore can be maintained. This is discussed with reference to the results of a simulation, the effect of which is discussed below.

Figure 7:
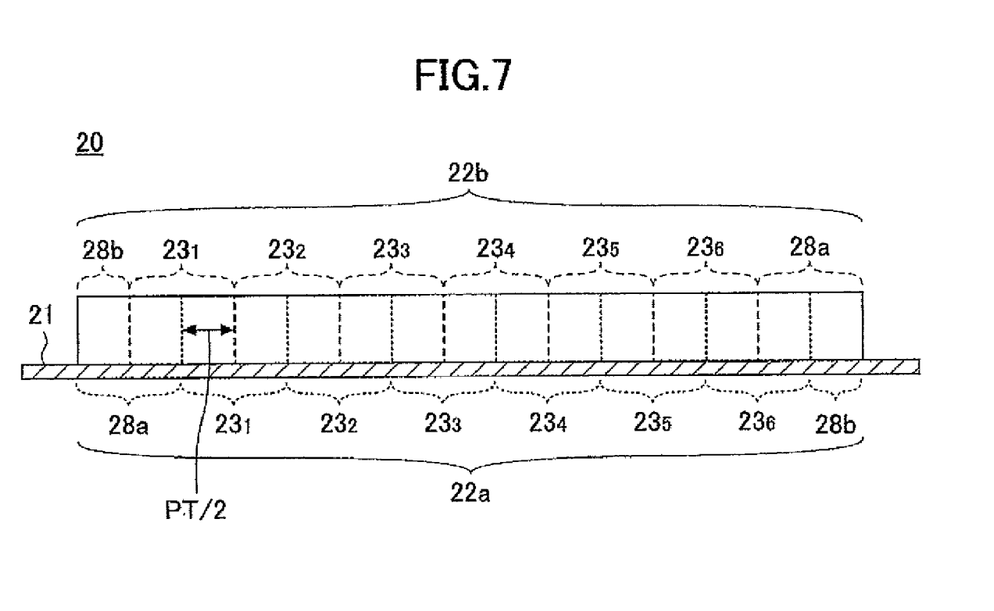
FIG. 7 is a schematic front view of the semiconductor detector.

FIG. 7 is a schematic front perspective view of the semiconductor detector 20. In FIG. 7, illustrations of the first electrode, the second electrode and the conductive adhesive layers are omitted.

The illustration in FIG. 7 is seen from the front surface (entry side of the gamma ray) side of the semiconductor detector 20. The semiconductor detection devices $23_1$ through $23_6$ of the first semiconductor detection device array 22a and the semiconductor detection devices $23_1$ through $23_6$ of the second semiconductor detection device array 22b are overlapped so that it looks as though the semiconductor detection devices 23 with gaps of PT/2 are arranged in a line. Two kinds of gamma rays, a gamma ray configured to generate an electron-hole pair in the first semiconductor detection device array 22a and a gamma ray configured to penetrate through the first semiconductor detection device array 22a so as to generate an electron-hole pair in the second semiconductor detection device array 22b, probabilistically exist. Because of this, for the gamma rays, the semiconductor detection device arrays 22a and 22b are, as shown in FIG. 7, substantially the same as the state where the semiconductor detection devices 23 are arranged in a line with the gap PT/2. Because of this, it can be presumed that the spatial resolution of the center of the visual field of the semiconductor detector 20 is close to the spatial resolution when the gaps of the semiconductor detection devices 23 are ½ of the gap PT. It is presumed that this contributes to improvement of the spatial resolution of the periphery part of the visual field of the semiconductor detector 20.

According to the first embodiment of the present invention, the semiconductor detector 20 has the detection efficiency and the spatial resolution substantially the same as that of a comparison example semiconductor detection device discussed below.

In other words, in the comparison example semiconductor detection device, the semiconductor detection devices 23 having a gap that is ½ of the gap PT are used and positions of the first semiconductor detection device array 22a and the second semiconductor detection device array 22b are maintained without modification. In the comparison example semiconductor detector, since the gap of the semiconductor detection devices 23 is PT/2, the number of the semiconductor detection devices is twenty four (24) and therefore twice the number of the semiconductor detectors 20 of the first embodiment of the present invention. Accordingly, in the semiconductor detector 20 of the first embodiment of the present invention compared to the comparison example semiconductor detector, the number of the semiconductor detection devices 23 can be decreased. As a result of this, since the number of the detection circuits connected to the semiconductor detection devices 23 or downstream circuits can be decreased, it is possible to prevent the increase of manufacturing costs such as material costs and assembly costs accompanied by an improvement the spatial resolution. In addition, the semiconductor detector 20 of the first embodiment compared to the comparison example semiconductor detector is wide. In other words, since the semiconductor detection device 32 is wide, manufacturing processes of the semiconductor detection device 23 such as cutting from the semiconductor wafer or a polishing process can be made easy. This contributes to the reduction of the manufacturing costs. In addition, it is possible to easily manufacture the semiconductor detection device array 22.

As shown in FIG. 5, the first semiconductor detection device array 22a and the second semiconductor detection device array 22b are arranged so as to be separated from each other at a distance DE in the depth direction (Y-axial direction). With this structure, after the first semiconductor detection device array 22a is arranged on the wiring board 21 in the assembling step, when the second semiconductor detection device array 22b is arranged, a tool for holding the second semiconductor detection device array 22b can use the space indicated by an arrow DE in FIG. 5. Hence, it is possible to easily arrange the semiconductor detection device array 22b. Even if the second semiconductor detection device array 22b is arranged and then the first semiconductor detection device array 22a is arranged, it is possible to achieve the same effect.

Next, a manufacturing step of the semiconductor detector 20 is discussed with reference to FIG. 8 and FIG. 5.

Figure 8:
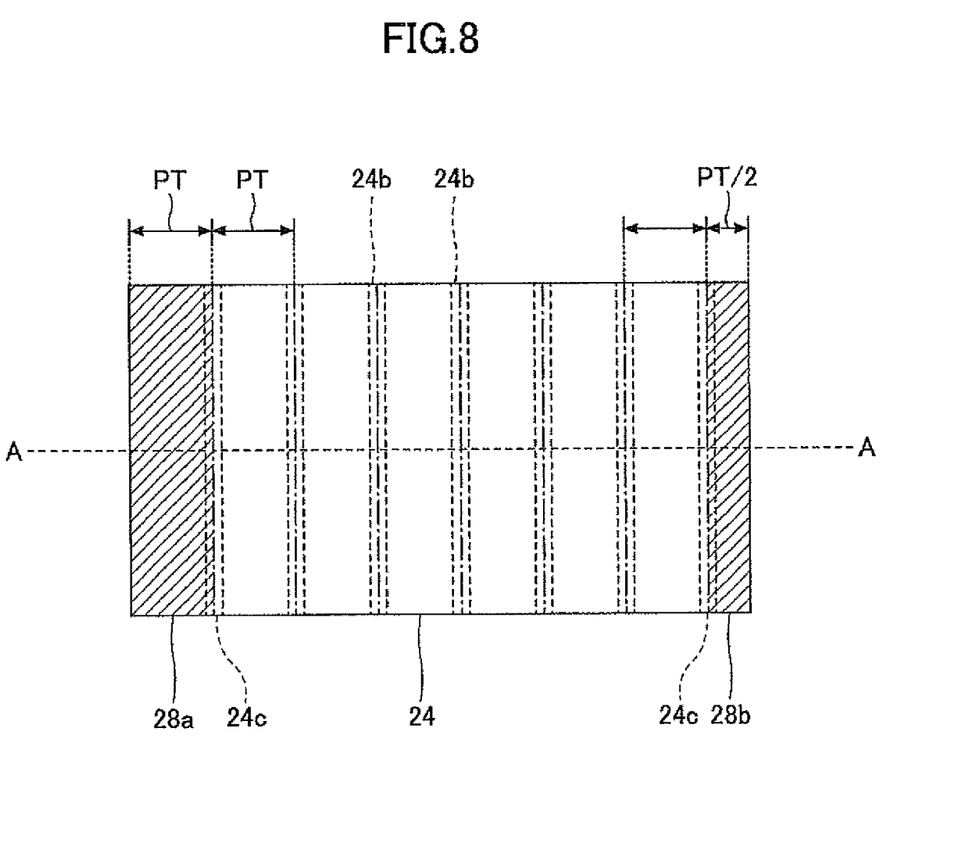
FIG. 8 is a view showing some of the manufacturing steps of first and second semiconductor detection device arrays.

FIG. 8 is a plan view showing a part of manufacturing steps of the first and second semiconductor detection device arrays 22a and 22b.

As semiconductor crystalline substrates of the first semiconductor detection device array 22a and the second semiconductor detection device array 22b, material having a length twice the depth or longer of one of the semiconductor detection device arrays 22 is used.

Referring to FIG. 8, first, the first electrode 25 is formed on an entire surface of a semiconductor crystal plate where the semiconductor crystalline substrate 24 and the guard members 28a and 28b are formed, and the second electrode 26 is formed on an entire other surface of the semiconductor crystal plate. The first electrode 25 and the second electrode 26 are formed by a vacuum deposition method or sputtering method.

Next, the groove parts 24b and 24c are formed with a designated gap at the second electrode side of the semiconductor crystal plate where the first electrode 25 and the second electrode 26 are formed. As a result of this, the semiconductor crystalline substrate 24 and the guard members 28a and 28b are formed.

Next, the structural body shown in FIG. 8 is cut in a designated depth position (line A-A), so that the first semiconductor detection device array 22a and the second semiconductor detection device array 22b are obtained.

Next, by using an assembly robot having a two-dimensional or three-dimensional motion or the like, end parts of the semiconductor detection device arrays 22a and 22b are positioned in the standard position along line Xa-Xa shown in FIG. 5. Then, the wiring board 21 is arranged and fixed.

The second semiconductor detection device array 22b is arranged by reversing the structural body shown in FIG. 8 so that it is not necessary to separately manufacture the first semiconductor detection device array 22a and the second semiconductor detection device array 22b. Hence, it is possible to easily manufacture the first semiconductor detection device array 22a and the second semiconductor detection device array 22b at low cost. In addition, since the same steps are applied to the first semiconductor detection device array 22a and the second semiconductor detection device array 22b until the cutting step is performed, it is possible to manufacture the first and second semiconductor detection device arrays 22a and 22b having the substantially same quality. Here, adhesion of the second electrodes 26 of the semiconductor detection device arrays 22a and 22b to the wiring board 21 can be made by electrical connection and fixing using, for example, a silver paste.

It is preferable to arrange the first semiconductor detection device array 22a and the second semiconductor detection device array 22b separated from each other in depth directions. Since a space where the tool for holding the first semiconductor detection device arrays 22a and the 22b of the assembly robot enters is secured, it is possible to easily perform the assembling step. Then, the first electrode 25 and the wiring board 21 can be connected by wire bonding 35. Thus, the semiconductor detector 20 is formed.

According to the above-discussed manufacturing method, in the case where the semiconductor detection device arrays 22a and 22b are positioned on the wiring board 21, the semiconductor detection device arrays 22a and 22b can be easily arranged by shifting the gap PT of the semiconductor detection devices at ½ patch by only positioning the end parts of the semiconductor detection device arrays 22a and 22b. In addition, since the lengths of the semiconductor detection device arrays 22a and 22b are the substantially equal to each other, only a single tool for holding the semiconductor detection device arrays 22a and 22b of the assembly robot is required so that the manufacturing cost can be reduced. Not only the above-mentioned method but also other known methods can be used as steps of assembling the semiconductor detector 20.

Second Embodiment

A PET apparatus of a second embodiment of the present invention is discussed. The PET apparatus of the second embodiment of the present invention is a modified example of the PET apparatus of the first embodiment of the present invention and an example where the number of the semiconductor detection device arrays 22 of the semiconductor detector 20 shown in FIG. 4 and FIG. 5 is expanded to "n". The semiconductor detector of the second embodiment of the present invention is the same as the semiconductor detector shown in FIG. 4 and FIG. 5 except for the number and arrangement of the semiconductor detection device arrays 22.

Figure 9:
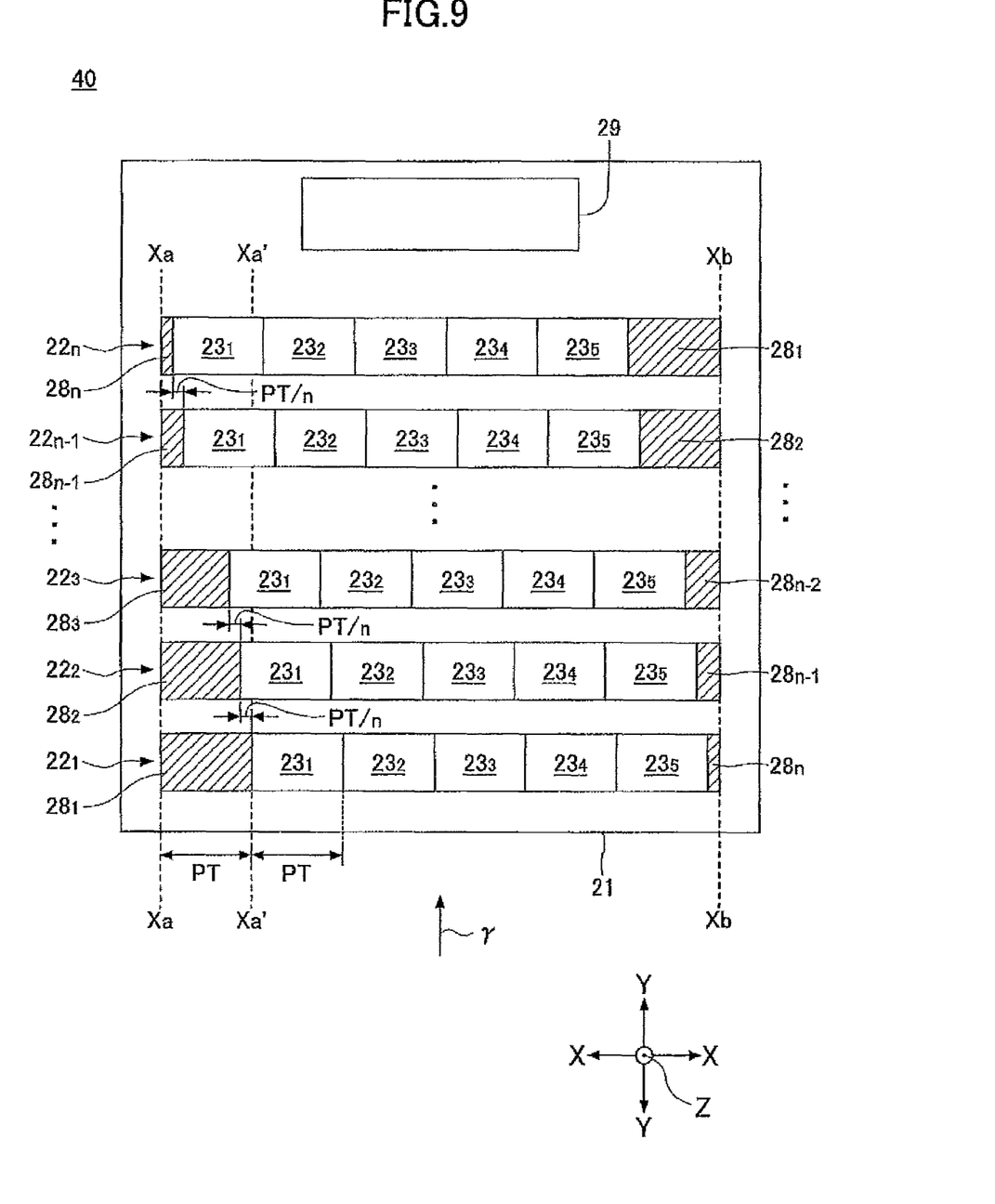
FIG. 9 is a schematic plan view of a semiconductor detector forming a PET apparatus of a second embodiment of the present invention.

FIG. 9 is a schematic plan view of a semiconductor detector 40 forming a PET apparatus of the second embodiment of the present invention. In FIG. 9, parts that are the same as the parts shown in FIG. 1 through FIG. 8 are given the same reference numerals, and explanation thereof is omitted.

Referring to FIG. 9, the semiconductor detector 40 includes the wiring board 21, semiconductor detection device arrays $22_1$ through $22_n$ provided on the wiring board 21, the connector 29 configured to transmit the output of the semiconductor detector 40 to the detection circuit (not shown in FIG. 9), and others. The value of "n" is selected from integer numbers greater than three. The semiconductor detection device arrays $22_1$ through $22_n$ each include five square pole-shaped semiconductor detection devices $23_1$ through $23_5$ and the guard members $28_1$ through $28_n$ provided one at each side in the arrangement direction of the semiconductor detection devices $23_1$ through $23_5$.

The semiconductor detection device arrays $22_1$ through $22_n$ (n lines of the semiconductor detection device arrays 22) are arranged in the depth direction (Y-axial direction) from the front side to the deep side. The guard members discussed below are provided so that a left end of each of the semiconductor detection device arrays $22_1$ through $22_n$ is consistent with the reference line Xa-Xa. The length in the arrangement direction of the guard members $28_1$, $28_2$, $28_3$, ..., $28_{n-1}$, $28_n$ is n/n, (n−1)/n, (n−2)/n, ..., 2/n, 1/n of the gap PT of the semiconductor detection device array 22.

Therefore, if another reference line Xa'-Xa' instead of the reference line Xa-Xa is provided at the left end of the semiconductor detection device $23_1$ of the first line semiconductor detection device array $22_1$, the left ends of the semiconductor detection device $23_1$ of semiconductor detection device array $22_1$ of the first, second, ..., (n−1)th, and nth lines are positioned at 0/n, 1/n, ..., (n−1)/n of the gap PT from the reference line Xa'-Xa'. Thus, the left ends of the semiconductor detection device $23_1$ of the semiconductor detection device arrays $22_1$ through $22_n$ of the first line through nth line are arranged so as to shift to the left side at PT/n in order.

Thus, in the second embodiment of the present invention, it is possible to achieve the same effect as the first embodiment of the present invention by arranging the semiconductor detection device arrays $22_1$ through $22_n$.

In other words, the semiconductor detector 40 of the second embodiment of the present invention maintains the detection efficiency substantially equal to that in the case where a single semiconductor detection device array 22 is provided and the depth of the semiconductor detection device is substantially equal to the sum of the depths of the semiconductor detection device arrays $22_1$ through $22_n$. The semiconductor detector 40 has much better spatial resolution that that of the semiconductor detection device arrays 22a and 22b. Hence, the number of the semiconductor detection devices 23 can be decreased so that the manufacturing cost can be reduced.

In addition, the semiconductor detector 40 of the second embodiment of the present invention can be formed by n lines of the semiconductor detection device arrays $22_1$ through $22_n$. Hence, it is possible to increase the gaps of the semiconductor detection devices 23, namely the length in the arrangement direction of the semiconductor detection devices 23, while the spatial resolution is maintained. In this case, it is preferable that the ratio of the gap PT of the semiconductor detection devices $23_1$ through $23_5$ and n (PT/n) be equal to or greater than 0.5 mm and equal to or smaller than 1.0 mm. This is because, even if PT/n is smaller than 0.5 mm, substantial improvement of substantial spatial resolution is not expected and also the number of the semiconductor detection device 23 is increased. That is to say, in a case where a positron is generated from the radioisotope, since the positron has kinetic energy, the positron is shifted $\frac{1}{10}$ of several mm from the position of the radioisotope. Since this shift cannot be avoided, even if PT/n is smaller than 0.5 μm, this does not substantially contribute to the improvement of the spatial resolution. Furthermore, if PT/n exceeds 1.0 mm, while the gap PT of the semiconductor detection device is increased, the spatial resolution is not sufficiently improved.

Next, in order to show the effect of the present invention, the PET apparatus of the embodiment of the present invention is simulated. Although the PET apparatus used in the simulation is that in the first embodiment of the present invention, the effect can be achieved by the PET apparatus of the second embodiment of the present invention.

Figure 10:
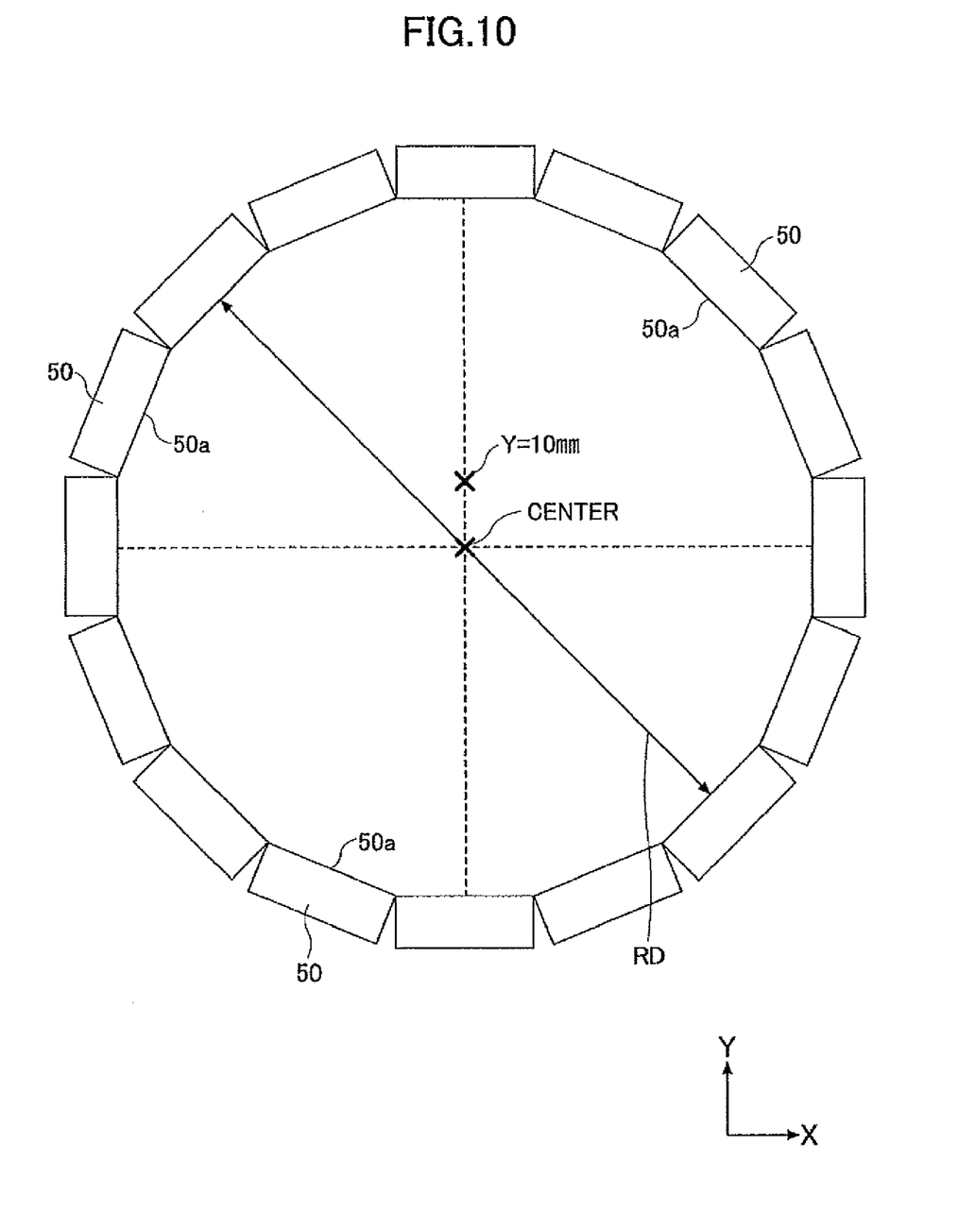
FIG. 10 is a schematic plan view showing an arrangement of the semiconductor detectors of the PET apparatuses of the embodiment and a comparison example.

FIG. 10 is a schematic plan view showing an arrangement of the semiconductor detectors of the PET apparatuses of the embodiment and a comparison example.

Referring to FIG. 10, the PET apparatus used in the simulation has a structure where 16 semiconductor detectors 50 are arranged around the center. The entrance surfaces 50a of the semiconductor detectors 50 are situated on the circumference having a diameter RD of 114.6 mm.

The semiconductor detector of this example, as well as the semiconductor detector 20 shown in FIG. 5, includes the first semiconductor detection device array and the second semiconductor detection device array. Each of the semiconductor detection devices are arranged so as to shift at ½ of the gap PT. Each of the first and second semiconductor detection device arrays includes 16 semiconductor detection devices. The semiconductor detection device has a width of 19.2 mm, a depth of 5 mm, a thickness of 1 mm, and a gap of the semiconductor detection devices of 1.2 mm. The gap between the first semiconductor detection device array and the second semiconductor detection device array is 5 mm. The number of the semiconductor detection devices of the example is 32.

On the other hand, a semiconductor detection of a comparison example 1 not using the present invention has a single semiconductor detection device array having 32 semiconductor detection devices. The semiconductor detection device has a width of 19.2 mm a depth of 10 mm, a thickness of 1 mm, and a gap of the semiconductor detection devices of 0.6 mm.

A semiconductor detection of a comparison example 2 not using the present invention has a single semiconductor detection device array having 32 semiconductor detection devices. The semiconductor detection device has a width of 19.2 mm, a depth of 5 mm, a thickness of 1 mm, and a gap of the semiconductor detection devices of 0.6 mm.

A case where gamma radiation sources are situated in the center of the 16 semiconductor detectors 50 and a case where gamma radiation sources are situated in positions shifted at 10 mm in the Y-axial direction (Y=10 mm) from the center are simulated in the example and the comparison examples 1 and 2. The simulation is performed according to the evaluation guidelines of the Japan Industries Association of Radiological Systems and uses $^{18}$F as a radiation element.

Figure 11:
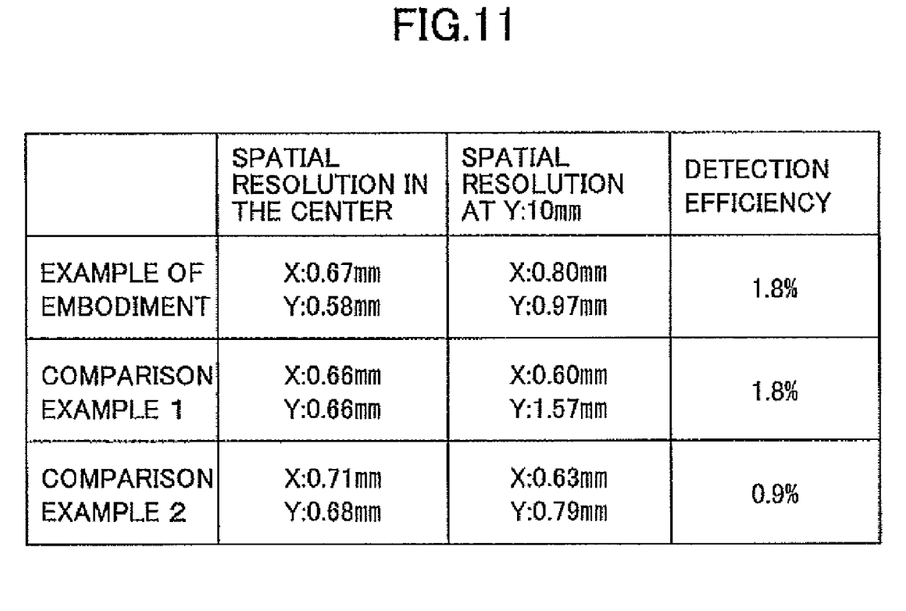
FIG. 11 is a table showing a simulation result of an example of the embodiment and comparison examples.

FIG. 11 is a table showing a simulation result of the example of the embodiment and comparison examples.

Referring to FIG. 11, in the example, although the width of the semiconductor detection device is twice that of the comparison example 1, the spatial resolution in the center of the example is substantially equal to that of the comparison example 1. This is because the semiconductor detection devices of each of the first and second semiconductor detection device arrays are shifted at ½ pitch. In a case of Y=10 mm, the spatial resolution in the Y-axial direction of the example compared to the comparison example 1 is drastically improved so that the spatial resolution in the X-axial direction and the Y-axial direction is smaller than 1.0 mm.

In addition, it is found that the detection efficiency of the example is higher than that of the comparison example 2. The detection efficiency is a coincidence sensitivity and ratio of pair annihilation gamma-rays which are coincidence-detected against a pair of annihilation gamma-rays which enters the radiation detector. The coincidence sensitivity is a value calculated from a coincidence probability determined by a solid angle of each semiconductor device seen from the center and the depth of each of the semiconductor devices.

Accordingly, it is found that although the number of the semiconductor detection devices in the example is the same as those of the comparison examples 1 and 2, the spatial resolution in the Y-axial direction is in the case of Y=10 mm drastically improved in the example compared to the comparison example 1 while the detection efficiency is maintained in the examples so that the spatial resolution is evenly improved in the entire visual field of the semiconductor detector in this example.

Thus, in the example compared to the comparison examples 1 and 2, it is possible to maintain the detection efficiency and improve the spatial resolution without increasing the number of the semiconductor detection devices. Therefore, in the example compared to the comparison examples 1 and 2, it is possible to maintain the detection efficiency and improve the spatial resolution without an increase of the manufacturing cost due to an increase in the number of the detection circuits connected to the semiconductor detection device or downstream circuits.

Thus, according to the embodiments of the present invention, it is possible to provide a radiation detector, including: a semiconductor detector including a plurality of semiconductor detection devices configured to generate electron-hole pairs based on entry of the radiation, wherein the semiconductor detector included n number of semiconductor detection device arrays provided on a board, the plural semiconductor detection devices are arranged in a first direction with a designated gap, the n number of the semiconductor detection device arrays are arranged in a second direction perpendicular to the first direction to form a $1^{st}$ line through an nth line, and the semiconductor detection device arrays of the $1^{st}$ line through the nth line are shifted at any of 0, 1/n, ..., (n−1)/n of the designated gap from a reference position in the first direction, where n is an integer number and equal to or greater than 2.

According to the above-mentioned ration detector, the semiconductor detector including n number of semiconductor detection device arrays provided on a board, the plural semiconductor detection devices are arranged in a first direction with a designated gap, the n number of the semiconductor detection device arrays are arranged in a second direction perpendicular to the first direction to form a $1^{st}$ line to an nth line, and the semiconductor detection device arrays of the $1^{st}$ line to the nth line are shifted at any of 0, 1/n, ..., (n−1)/n of the designated gap from a reference position in the first direction, where n is an integer number equal to or greater than 2. Since the sum of the lengths in the second directions of the $1^{st}$ line through nth line of the semiconductor detection device arrays is equal to the length in the second direction of the conventional single line of the semiconductor detection device array, it is possible to maintain the detection efficiency and improve the spatial resolution of the periphery of the visual field. In addition, since the semiconductor detection devices of the $1^{st}$ line through nth line are arranged so as to be shifted at 1/n of the designated gap, the spatial resolution of the center of the visual field can be improved compared to a case where the semiconductor detection devices of the $1^{st}$ line through nth line are not shifted. Accordingly, it is possible to make the designated gap of the semiconductor detection devices wider than the semiconductor detection device array having the spatial resolution equal to the conventional one. As a result of this, it is possible to increase the width of the semiconductor detection device and decrease the number of the semiconductor detection devices. Accordingly, it is possible to maintain the detection efficiency, improve the spatial resolution of the periphery of the visual field, and prevent the increase of the manufacturing cost.

The semiconductor detection arrays may be arranged so as to be shifted at 1/n of the designated gap from the first line through the nth line in order. Each of the semiconductor detection device arrays may include m number of the semiconductor detection devices, and in two semiconductor detection device arrays neighboring along the second line, each of the semiconductor detection devices from the reference position to a kth position may be arranged so as to be shifted at 1/n of the designated gap, where m is an integer number equal to or greater than 2 and k is any one of 1 through m.

Each of the semiconductor detection device arrays of the $1^{st}$ line through the nth line may include a protection member situated at an end part in the first direction of the semiconductor detection device arrays so that the end parts are situated at the same length from the reference position. Each of the semiconductor detection device arrays of the $1^{st}$ line through the nth line may include another protection member situated at an opposite end part in the first direction of the semiconductor detection device arrays so that the length in the first direction of each of the semiconductor detection device arrays is equal to the others.

According to the above-mentioned radiation detector, it is possible to easily position the semiconductor detection devices of the $1^{st}$ line through nth line, and the positional relationship of the semiconductor detection devices can be easily realized.

The semiconductor detection device arrays may be separated from each other in the second direction.

According to the above-mentioned radiation detector, it is possible to secure the space where the jog for holding the semiconductor detection device array in the assembling step of the semiconductor detector. Hence, it is possible to secure the working abilities.

According to the embodiments of the present invention, it is also possible to provide a radiographic inspection apparatus, including: the above-mentioned radiation detector being configured to detect radiation generated from a subject including a radioisotope; and an information processing part configured to obtain distribution information of the radioisotope in the subject based on detection information, the detection information including entry time and entry position of the radiation obtained from the radiation detector.

According to the above-mentioned radiographic inspection apparatus, the radiation detector can maintain the detection efficiency, the spatial resolution in the entire visual field is good, and increase of the manufacturing cost is prevented. Accordingly, it is possible to perform the inspection with accuracy higher than the conventional art without an increase of the inspection time, and prevent the increase of the manufacturing cost.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority or inferiority of the invention. Although the embodiment of the present invention has been described in detail, it should be understood that various changes, substitutions, and alterations could be made hereto without departing from the spirit and scope of the invention.

For example, although the PET apparatus is discussed as an example of the present invention in the above discussed embodiments, the present invention is not limited to this. The present invention can be applied to a SPECT (single photon-emission computed tomography) apparatus. In addition, in the above-discussed embodiments, the case where the semiconductor detector detects the gamma ray is discussed as an example. However, the present invention can be applied to a semiconductor detector configured to detect X-rays or other radiation.

Furthermore, in the first and second embodiments of the present invention, as shown in FIG. 5 and FIG. 9, the semiconductor detector is formed of the semiconductor detection device arrays provided on a single wiring board. However, the semiconductor detector may be formed of the semiconductor detection device arrays provided on each of two or more wiring boards.

This application claims priority to Japanese Patent Application No. 2006-124653 filed in Japan on Apr. 28, 2006. The foregoing application is hereby incorporated herein by reference.

INDUSTRIAL APPLICABILITY

The present invention is applicable to radiation detectors and radiographic inspection apparatuses. More specifically, the present invention is applicable to a radiation detector configured to detect gamma rays emitted from a radioisotope situated in a subject and a radiographic inspection apparatus.

The invention claimed is:

1. A radiation detector, comprising:
a semiconductor detector including a plurality of semiconductor detection devices configured to generate electron-hole pairs based on entry of the radiation,
wherein the semiconductor detector includes n number of semiconductor detection device arrays, each of which is formed of semiconductor crystalline substrate, provided on a board,
the plural semiconductor detection devices are arranged in a first direction with a designated gap,
the n number of the semiconductor detection device arrays are arranged in a second direction perpendicular to the first direction to form a $1^{st}$ line through an nth line,
the semiconductor detection device arrays of the $1^{st}$ line through the nth line are arranged in order from the $1^{st}$ line to the nth line so as to be shifted at any of $0, 1/n, \ldots, (n-1)/n$ of the designated gap from a reference position in the first direction, where n is an integer number and equal to or greater than 2,
each of the semiconductor detection device arrays of the $1^{st}$ line through the nth line includes a protection member situated at an end part in the first direction of the semiconductor detection device arrays so that the end parts are situated at the same length from the reference position, and
a groove part is formed between said protection member and one of said semiconductor detection devices adjacent to said protection member.

2. The radiation detector as claimed in claim 1,
wherein the semiconductor detection arrays are arranged so as to be shifted at 1/n of the designated gap from the first line through the nth line in order.

3. The radiation detector as claimed in claim 1,
wherein each of the semiconductor detection device arrays includes m number of the semiconductor detection devices,
in two semiconductor detection device arrays neighboring along the second line, each of the semiconductor detection devices from the reference position to a kth position is arranged so as to be shifted at 1/n of the designated gap, where m is an integer number equal to or greater than 2 and k is any one of 1 through m.

4. The radiation detector as claimed in claim 1,
wherein each of the semiconductor detection device arrays of the $1^{st}$ line through the nth line includes another protection member situated at an opposite end part in the first direction of the semiconductor detection device arrays so that the length in the first direction of each of the semiconductor detection device arrays is equal to the others.

5. The radiation detector as claimed in claim 1,
wherein the semiconductor detection device arrays are separated from each other in the second direction.

6. The radiation detector as claimed in claim 1,
wherein, in a case where the designated gap is denoted by PT, the ratio of PT and n (PT/n) is equal to or greater than 0.5 mm and equal to or smaller than 1.0 mm.

7. The radiation detector as claimed in claim 1,
wherein n is equal to 2, and
the semiconductor detection devices of the semiconductor detection device array of the $1^{st}$ line are positioned so as to be shifted at ½ of the designated gap.

8. A radiographic inspection apparatus, comprising:
the radiation detector claimed in claim 1, the radiation detector being configured to detect radiation generated from a subject including a radioisotope; and
an information processing part configured to obtain distribution information of the radioisotope in the subject based on detection information, the detection information including entry time and entry position of the radiation obtained from the radiation detector.

* * * * *